United States Patent
Gray et al.

(10) Patent No.: US 6,929,638 B2
(45) Date of Patent: Aug. 16, 2005

(54) EYE REGISTRATION AND ASTIGMATISM ALIGNMENT CONTROL SYSTEMS AND METHOD

(75) Inventors: Gary Paul Gray, Orlando, FL (US); John Alfred Campin, Orlando, FL (US); Qiping Shen, Lake Mary, FL (US)

(73) Assignee: Alcon RefractiveHorizons, Inc., Fort Worth, TX (US)

( * ) Notice: Subject to any disclaimer, the term of this patent is extended or adjusted under 35 U.S.C. 154(b) by 0 days.

(21) Appl. No.: 10/733,867

(22) Filed: Dec. 11, 2003

(65) Prior Publication Data

US 2004/0143244 A1 Jul. 22, 2004

Related U.S. Application Data

(63) Continuation-in-part of application No. 09/838,665, filed on Apr. 19, 2001, now Pat. No. 6,702,806.
(60) Provisional application No. 60/270,071, filed on Feb. 20, 2001, and provisional application No. 60/198,393, filed on Apr. 19, 2000.

(51) Int. Cl.[7] .......................... A61N 5/01; A61N 5/067
(52) U.S. Cl. ........................................................ 606/5
(58) Field of Search ........................ 606/4–6; 351/208

(56) References Cited

U.S. PATENT DOCUMENTS

| | | | |
|---|---|---|---|
| 4,476,862 A | 10/1984 | Pao | |
| 4,523,821 A | 6/1985 | Lang et al. | |
| 4,579,430 A | 4/1986 | Bille | |
| 4,632,528 A | 12/1986 | Yoshino et al. | |
| 4,669,466 A | 6/1987 | L'Esperance | |
| 4,688,941 A | 8/1987 | Philbert | |
| 4,705,035 A | 11/1987 | Givens | |
| 4,718,418 A | 1/1988 | L'Esperance, Jr. | |
| 4,739,761 A | 4/1988 | Grandon | |
| 4,848,340 A | 7/1989 | Bille et al. | |
| 5,029,220 A | 7/1991 | Juday | |
| 5,098,426 A | 3/1992 | Sklar et al. | |
| 5,196,873 A | 3/1993 | Yamanobe et al. | |
| 5,303,709 A | 4/1994 | Dreher et al. | |
| 5,354,281 A | 10/1994 | Chen | |
| 5,485,404 A | 1/1996 | Shindo | |
| 5,531,753 A | 7/1996 | Oliveira | |
| 5,568,208 A | 10/1996 | Van de Velde | |
| 5,614,967 A | 3/1997 | Ishikawa et al. | |
| 5,620,436 A | 4/1997 | Lang et al. | |
| 5,632,742 A | 5/1997 | Frey et al. | |
| 5,638,176 A | 6/1997 | Hobbs et al. | |

(Continued)

FOREIGN PATENT DOCUMENTS

| | | |
|---|---|---|
| EP | 0 456 166 A1 | 11/1991 |
| WO | WO 98/00078 | 1/1998 |
| WO | WO 01/28476 A1 | 4/2001 |

Primary Examiner—Andrew M. Dolinar
(74) Attorney, Agent, or Firm—Allen, Dyer, Doppelt, Milbrath & Gilchrist, P.A.

(57) ABSTRACT

An orientation system and method for corrective eye surgery includes a camera for performing a first image mapping of a patient's eye using a predetermined eye feature and software for processing the first image map to determine an edge location of the feature. A second image mapping of the eye is performed with the patient in a different position. The second image map is processed to locate the predetermined eye feature. Correlation of the mappings is used to calculate an orientational change of the eye between the two positions. This procedure may also be performed at different times during surgery to permit "real-time" data on orientational changes undergone by the eye to be collected. In both cases the data are used to calculate an adjustment to be applied to a corrective prescription for application by the surgical procedure.

27 Claims, 10 Drawing Sheets

U.S. PATENT DOCUMENTS

| | | |
|---|---|---|
| 5,645,550 A | 7/1997 | Hohla |
| 5,684,545 A | 11/1997 | Dou et al. |
| 5,865,832 A | 2/1999 | Knopp et al. |
| 5,892,569 A | 4/1999 | Van de Velde |
| 5,923,399 A | 7/1999 | Van de Velde |
| 5,943,117 A | 8/1999 | Van de Velde |
| 5,966,197 A | 10/1999 | Yee |
| 6,000,799 A | 12/1999 | Van de Velde |
| 6,027,216 A | 2/2000 | Guyton et al. |
| 6,186,628 B1 | 2/2001 | Van de Velde |
| 6,394,999 B1 * | 5/2002 | Williams et al. ............ 606/5 |

* cited by examiner

EYE REGISTRATION AND ASTIGMATISM ALIGNMENT CONTROL SYSTEMS AND METHOD

CROSS-REFERENCE TO RELATED APPLICATION

This application is a continuation-in-part of application Ser. No. 09/838,665, filed Apr. 19, 2001, now U.S. Pat. No. 6,702,806 which itself claims priority from and incorporates by reference commonly owned provisional applications Ser. No. 60/198,393, filed Apr. 19, 2000, "Astigmatism Alignment Control Device and Method," and Ser. No. 60/270,071, filed Feb. 20, 2001, "Eye Registration Apparatus and Method."

BACKGROUND OF THE INVENTION

1. Field of the Invention

The present invention relates to systems and methods for improving objective measurements preceding corrective eye surgery, and, more particularly, to such systems and methods for improving results of corrective laser surgery on the eye.

2. Description of Related Art

Laser-in-situ-keratomileusis (LASIK) is a common type of laser vision correction method. It has proven to be an extremely effective outpatient procedure for a wide range of vision correction prescriptions. The use of an excimer laser allows for a high degree of precision and predictability in shaping the cornea of the eye. Prior to the LASIK procedure, measurements of the eye are made to determine the amount of corneal material to be removed from various locations on the corneal surface so that the excimer laser can be calibrated and guided for providing the corrective prescription previously determined by the measurements. Refractive laser surgery for the correction of astigmatism typically requires that a cylindrical or quasicylindrical ablation profile be applied to the eye. The long axis of this profile must be properly oriented on the eye in order to accurately correct the visual aberration.

An objective measurement of a patient's eye is typically made with the patient sitting in an upright position while focusing on a target image. A wavefront analyzer then objectively determines an appropriate wavefront correction for reshaping the cornea for the orientation of the eye being examined. The LASIK or PRK procedure is then typically performed with the patient in a prone position with the eye looking upward.

It is well known that the eye undergoes movement within the socket comprising translation and rotation ("cyclotorsion") as the patient is moved from the upright measuring position to the prone surgery position. Techniques known in the art for accommodating this movement have included marking the eye by cauterizing reference points on the eye using a cautery instrument (U.S. Pat. No. 4,476,862) or caustic substance, a very uncomfortable procedure for the patient. It is also known to mark a cornea using a plurality of blades (U.S. Pat. No. 4,739,761). The injection of a dye or ink is also used to mark the reference locations to identify the orientation of the eye during measurement, permitting a positioning of the corrective profile to the same orientation prior to surgery. However, the time delay from measurement to surgery often causes the ink to run, affecting the accuracy of an alignment. Making an impression on the eye (U.S. Pat. No. 4,705,035) avoids the caustic effects of cauterizing and the running effect of the ink. However, the impression loses its definition quickly relative to the time period between the measurement and surgery.

For correction of astigmatism, it is known to mark the cornea preparatory to making the surgical incisions (U.S. Pat. No. 5,531,753).

Tracker systems used during the surgical procedure or simply for following eye movement, while the patient is in a defined position, are known to receive eye movement data from a mark on a cornea made using a laser beam prior to surgery (U.S. Pat. No. 4,848,340) or from illuminating and capturing data on a feature in or on the eye, such as a retina or limbus (U.S. Pat. Nos. 5,029,220; 5,098,426; 5,196,873; 5,345,281; 5,485,404; 5,568,208; 5,620,436; 5,638,176; 5,645,550; 5,865,832; 5,892,569; 5,923,399; 5,943,117; 5,966,197; 6,000,799; 6,027,216).

SUMMARY OF THE INVENTION

A system and method are provided for accurately orienting an eye for surgery to the same orientation it had during an objective measurement. An orientation correction algorithm is provided to the software driving a corrective surgical device. Further, pairs of eye images taken at different times can be aligned (registered). The system and method also avoids placing a patient in an uncomfortable or harmful situation.

A first embodiment of the system of the present invention comprises means for performing a first image mapping of an eye of a patient situated in a first position using a predetermined eye feature. Means are further provided for performing a second image mapping of the eye of the patient in a second position different from the first position using the predetermined eye feature. Means are also provided for processing the first and the second image map to determine an edge location of the feature in two dimensions and to locate the predetermined eye feature. Finally, software means are included for calculating an orientational change to be applied to a corrective prescription for a surgical procedure to be performed on the eye with the patient in the second position. The procedure may comprise, for example, implementing a correction profile that had been determined with the patient in the first position with, for example, a wavefront analysis and conversion system for calculating an ablation profile for a cornea, such as described in copending and co-owned U.S. patent application Ser. No. 09/566,668, the disclosure of which is hereby incorporated by reference.

The method of this first embodiment of the present invention is for orienting a corrective program for eye surgery and comprises the steps of performing a first image mapping of an eye of a patient in a first position using a predetermined eye feature. The method also comprises the steps of performing a second image mapping of the eye of the patient in a second position different from the first position using the feature and processing the first and the second image map to determine an edge location of the feature in two dimensions and to locate the feature. Next an orientational change to be applied to a corrective prescription for a surgical procedure to be performed on the eye with the patient in the second position is calculated. The procedure comprises a correction profile determined with the patient in the first position.

Thus this aspect of the present invention provides a system and method for achieving a precise registration of the eye with a measurement of the movement of an eye feature. As a result, the prescription measurement for reshaping the cornea will account for the rotation and translation of the eye occurring between measurements made with the patient in a sitting position and laser surgery with the patient in a prone position.

An additional embodiment of the invention is directed to a system and method for orienting a corrective prescription for eye surgery. In this embodiment a first image map of an eye of a patient is processed at a first time during the surgery to produce a first edge image of the eye in two dimensions, and a second image map of the patient eye is processed at a second time during the surgery to produce a second edge image of the eye in two dimensions.

Two identifiable features are selected from one of the first and the second image maps, a location of the two features in the first and the second edge images is correlated. From the correlated locations is calculated an orientational change to be applied to a previously determined corrective prescription for a correction profile to be achieved on the eye during the surgery. Such a procedure can be carried out on a substantially continuous basis if desired to achieve substantially "real-time" adjustment to the corrective prescription.

Yet another embodiment of the orientation system for eye surgery for correcting astigmatism comprises means for making two alignment marks on an eye of a patient with the patient in a first position. Means are also provided for imaging the eye with the patient in a second position that is different from the first position. The system also comprises a computer that has input and output means. The input means are in electronic connection with the imaging means, and an operator input device is in electronic communication with the computer input means. Means for displaying the eye image to an operator are also in communication with the computer input and output means.

First software means are resident in the computer for superimposing a graphical reticle means onto the eye image on the displaying means and for permitting the graphical reticle means to be moved by the operator under control of the operator input means. The reticle means comprise a line for aligning with the two alignment marks. Second software means also resident in the computer are for calculating an orientational change to be applied to a corrective surgical procedure to be performed on the eye with the patient in the second position. As above, the procedure comprises a correction profile determined with the patient in the first position.

The features that characterize the invention, both as to organization and method of operation, together with further objects and advantages thereof, will be better understood from the following description used in conjunction with the accompanying drawings. It is to be expressly understood that the drawings are for the purpose of illustration and description and are not intended as a definition of the limits of the invention. These and other objects attained, and advantages offered, by the present invention will become more fully apparent as the description that now follows is read in conjunction with the accompanying drawings.

DETAILED DESCRIPTION OF THE PREFERRED EMBODIMENTS

A description of the preferred embodiments of the present invention will now be presented with reference to FIGS. 1–10.

Figure 1:
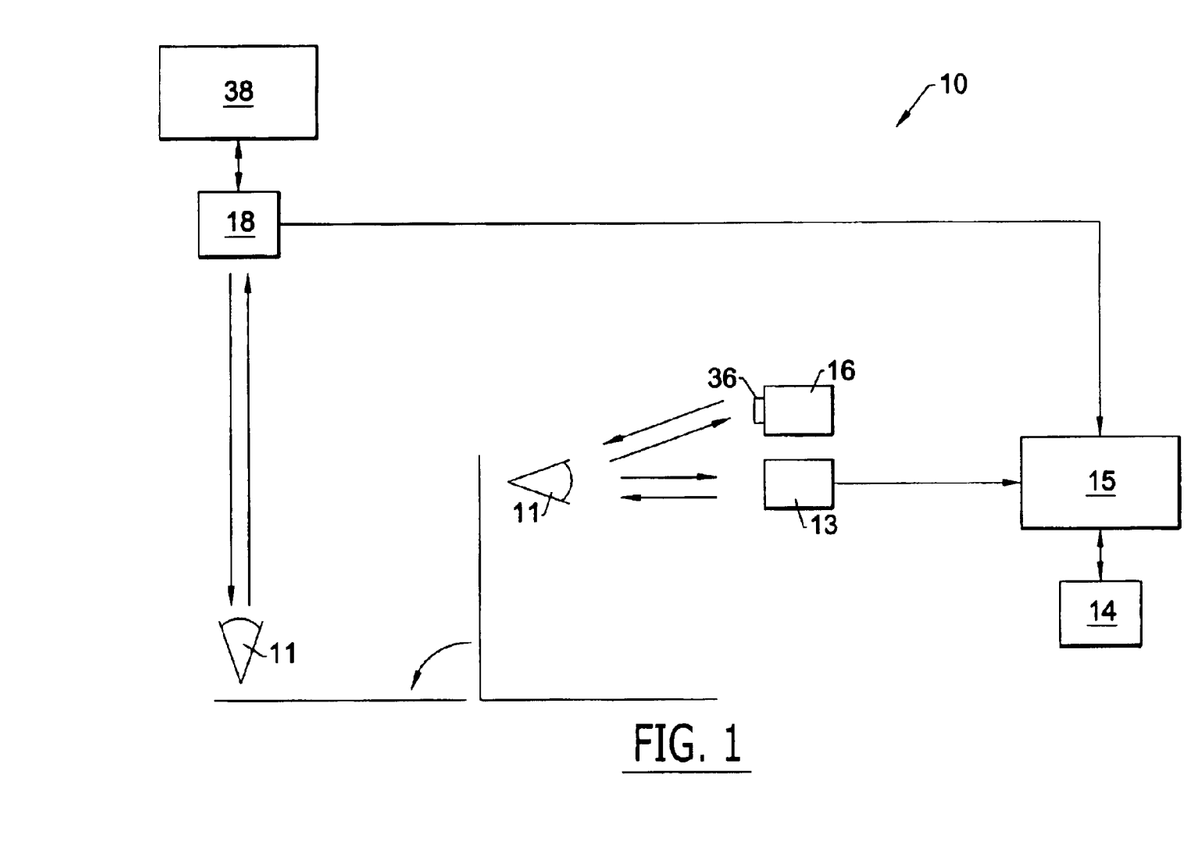
FIG. 1 is a schematic diagram of the system of a first embodiment of the present invention.
Figure 2:
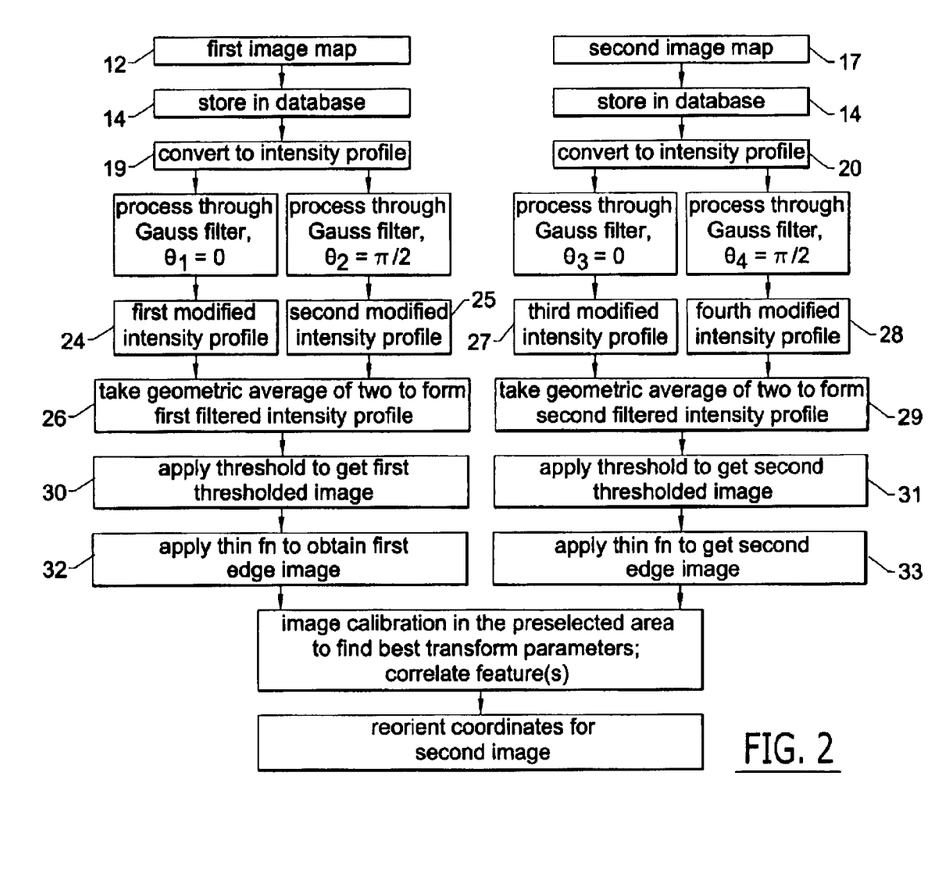
FIG. 2 is a block diagram of the data flow.
Figure 3:
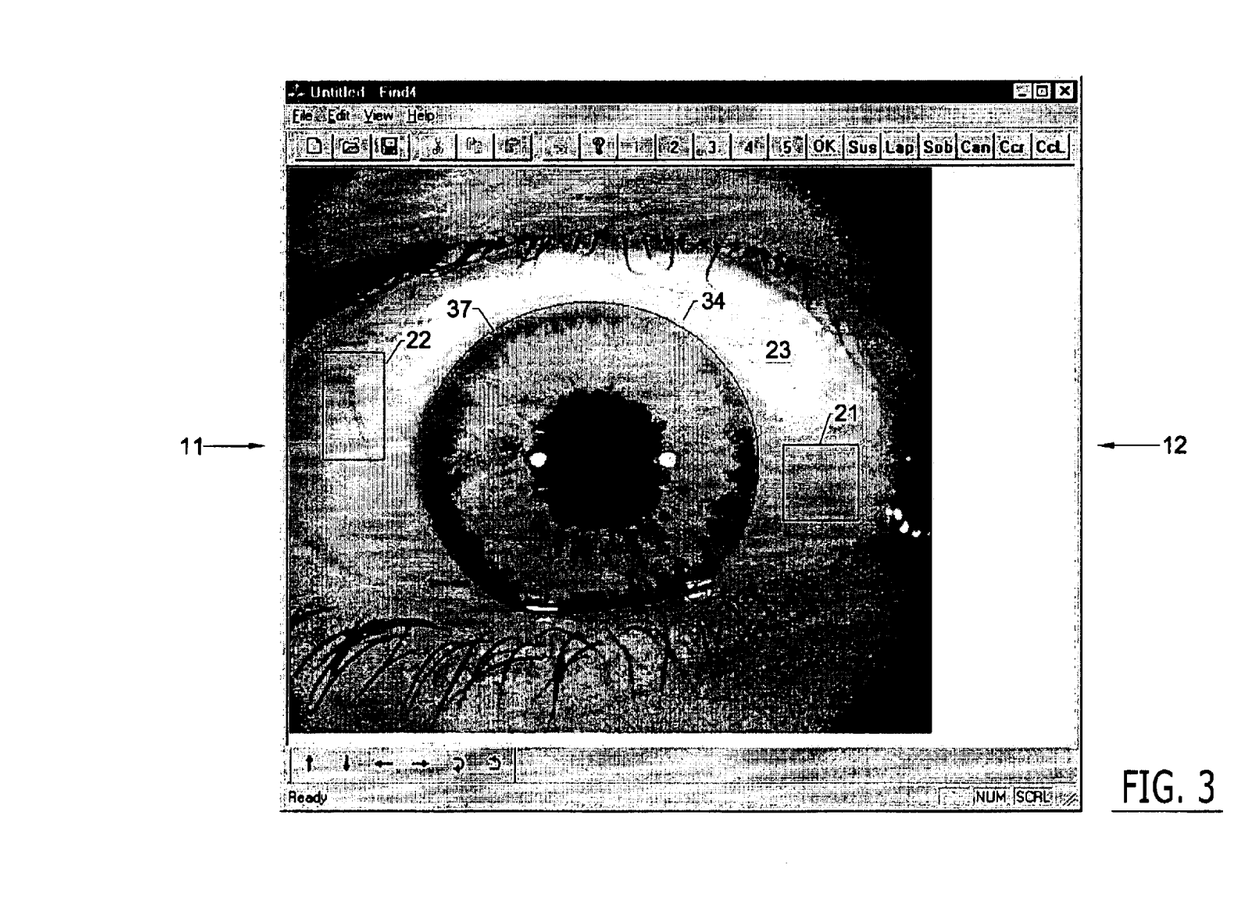
FIG. 3 is a view of the original image, before image processing, with feature boxes around the features to be used as registration regions.

A schematic diagram of a system 10 of a first embodiment of the invention is shown in FIG. 1, data flow and resulting images in FIG. 2, and original and processed images in FIGS. 3–8. A section on the image processing algorithms embodied herein follows the description of the system and method. In an exemplary embodiment of the system 10, a patient's eye 11 is image mapped in a substantially upright position by capturing a first video image 12 using a camera such as a charge-coupled-device (CCD) camera 13. Such an image 12 is illustrated in FIG. 3. The first image 12 is stored in a database 14 in electronic communication with a computer 15 and labeled as an original image from a first measurement.

Next an objective measurement is made on the eye 11 to determine a desired correction profile, using a measurement system 16 such as that disclosed in copending application Ser. No. 09/566,668, although this is not intended as a limitation.

Once the correction profile is determined, the patient is made ready for surgery, and placed in the second position, which is typically prone. Alternatively, the first scan to determine the correction profile may be made in a different location and at a time prior to the surgical procedure, the time interval being, for example, several weeks. Then a second image map 17 is collected using a second camera 18, in communication with a second system 38 for performing surgery, and these data are also stored in the database 14. In a preferred embodiment both the first 13 and the second 18 cameras are adapted to collect color images, and these images are then converted using software resident on the computer 15 to intensity profiles 19,20 as grey-scale images. Alternatively, color images may be used. It is useful to collect color images for viewing by the physician, since image mapping of the eye 11 may be made using preselected identifiable images such as blood vessels 21,22 typically seen within the sclera 23. In a color image, the red color of the vessels 21,22 is clearly identifiable. Typically the second image map 17 is collected during setup prior to surgery using a correction system such as is disclosed in application Ser. No. 09/566,668, although this is not intended as a limitation. As the image maps 12,17 are typically collected with different cameras 13,18, the qualities of the images 12,17 are expected to be different, making the image processing steps of great importance.

Figure 4:
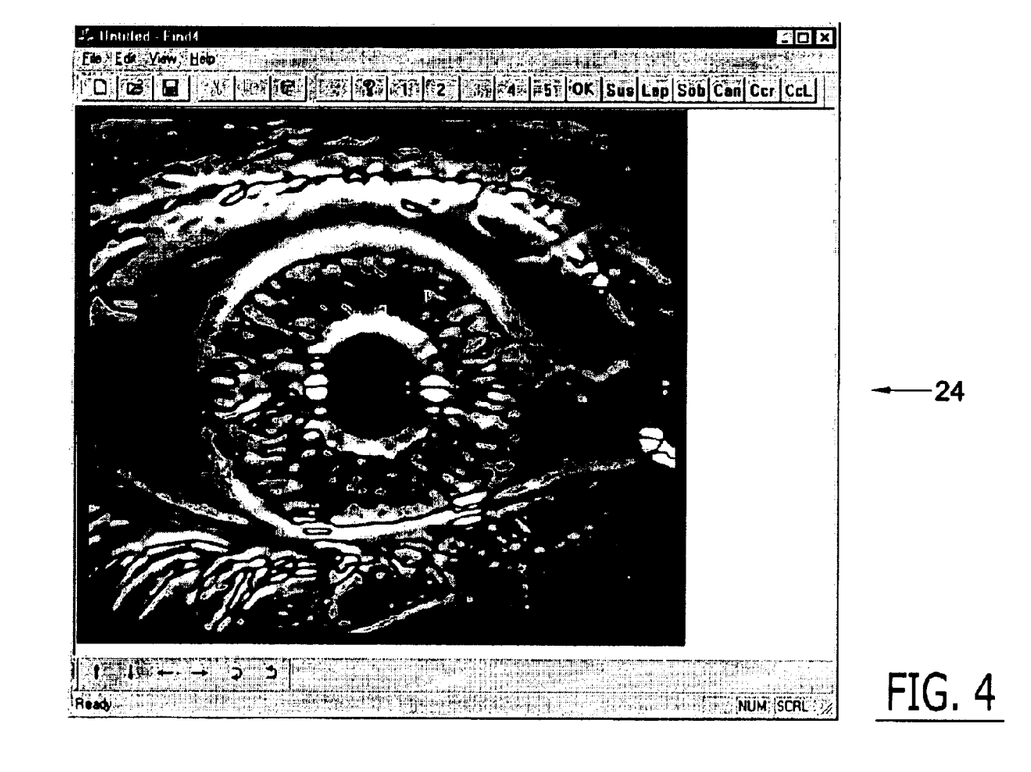
FIG. 4 is a view of a Gauss-filtered intensity profile with $\theta_1=0$, showing the edge in an x direction.
Figure 5:
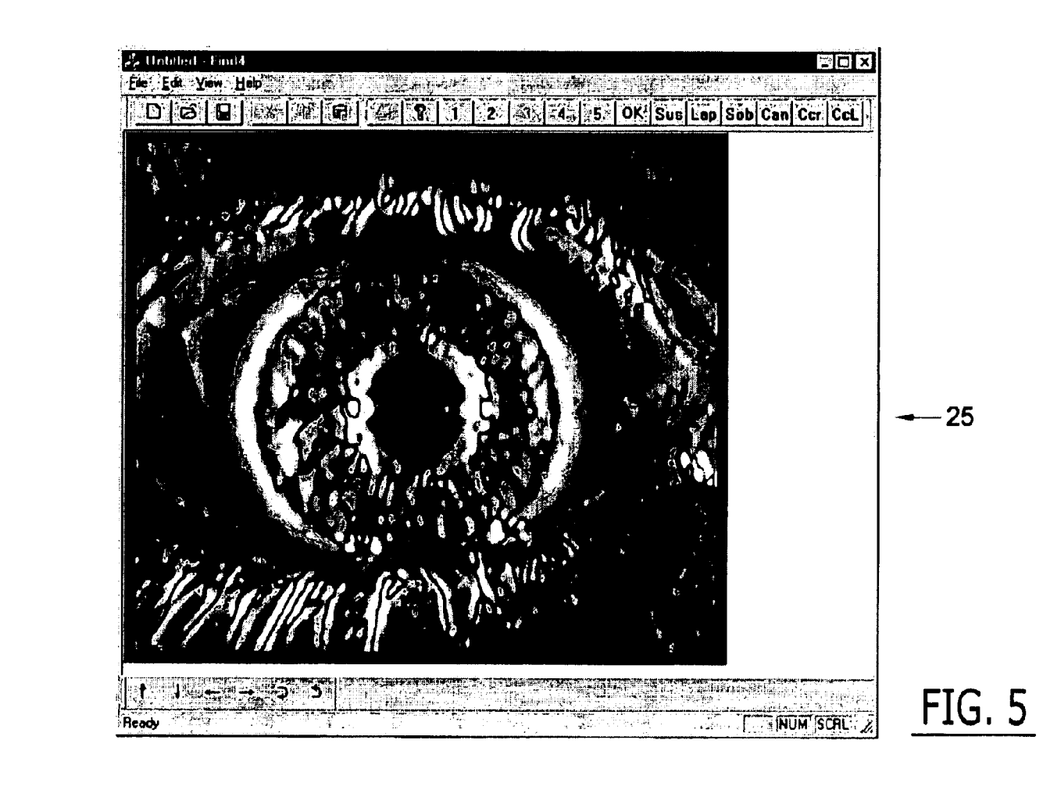
FIG. 5 is a view of a Gauss-filtered intensity profile with $\theta_2=\pi/2$, showing the edge in a y direction.

Next the intensity profile 19 of the first video image 12 is processed through a weighting function such as a filter, in a preferred embodiment a Gauss filter, although this is not intended as a limitation. This filter is for eliminating noise within the intensity profiles for defining image edge locations in both an x and a y orientation to provide two-dimensional information, and also to emphasize or highlight features for subsequent processing. The Gauss filter establishes a first modified intensity profile 24 with $\theta_1=0$, as an example, as shown in FIG. 4, an edge view in the x direction, the $\theta$ values taken relative to the x axis. The Gauss filter is again applied to the intensity profiles to establish a second modified intensity profile 25, with $\theta_2=\pi/2$, as shown in FIG. 5, an edge view in a y direction.

Figure 6:
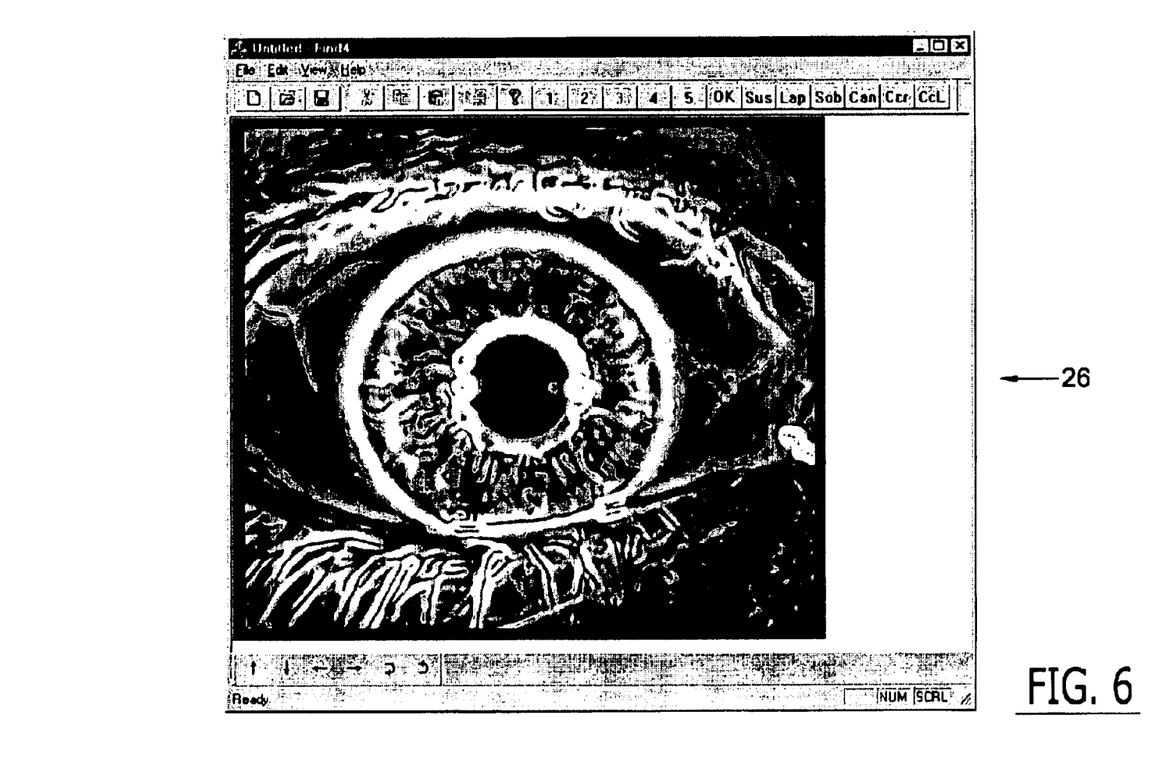
FIG. 6 is a view of a geometric average of FIGS. 4 and 5.

A geometric average of the filtered x and y orientations is performed and processed to eliminate unwanted noise levels to form a first filtered intensity profile 26 for the first image 12, yielding a view as shown in FIG. 6. This first filtered intensity profile 26 has been calculated by taking the square root of the sum of the squares of the first 24 and the second 25 modified intensity profiles.

The above process is repeated for the second image 17, to produce, from the second intensity profile 20, a third modified intensity profile 27 from application of a Gauss filter with $\theta_3=0$ and a fourth modified intensity profile 28, with $\theta_4=\pi/2$, and geometric averaging to produce a second filtered intensity profile 29.

Figure 7:
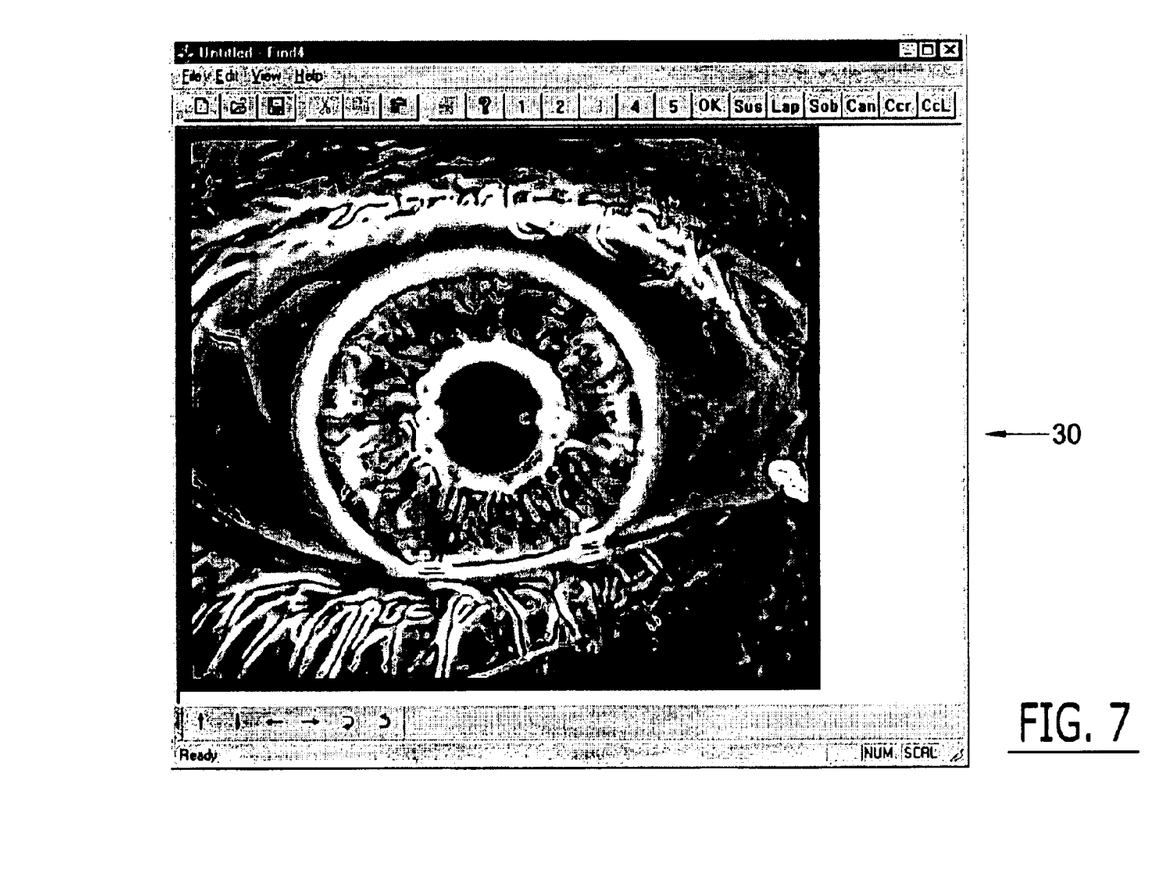
FIG. 7 is a view with threshold application.

Next an adaptive signal threshold is selected to reduce background noise for the first 26 and the second 29 filtered intensity profiles, resulting in first 30 and second 31 thresholded images, with the first thresholded image 30 shown in FIG. 7. The $\lambda$ may be different for the first 26 and the second 29 filtered intensity profiles; here $\lambda=0.03$.

Figure 8:
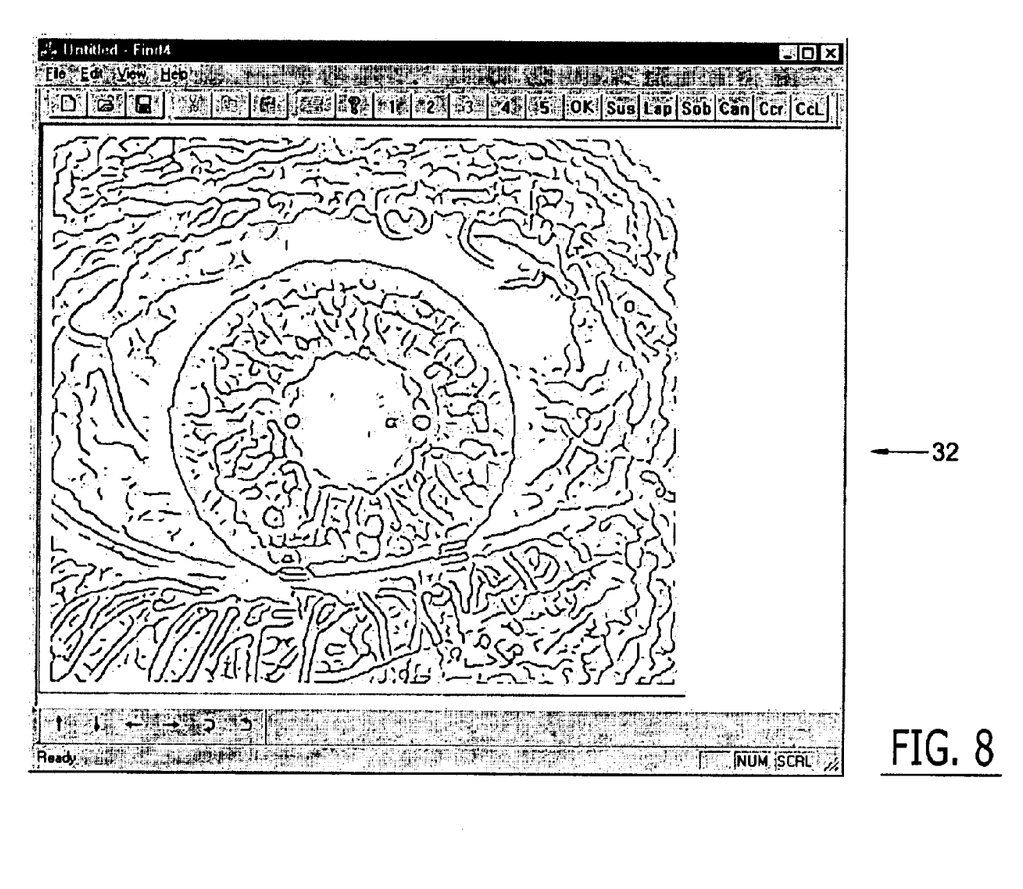
FIG. 8 is a view of the image following application of the thin function.

The first 26 and the second 29 filtered intensity profiles 26,29 are then processed through a "thin function" to produce a first 32 and a second 33 edge image, with the first edge image 32 shown in FIG. 8. This step completes the image processing. Next the surgeon selects one or more features in the eye 11, shown as a first 21 and a second 22 feature (here, blood vessels) in FIG. 3. The selected features are used for correlating between filtered images for the second (surgical) position of the eye 11 with that of the first (measurement) position. Other features may also be used if sufficiently prominent blood vessels are not present. The excimer laser 36 coordinates are then reoriented to accommodate the rotation and translation that took place when moving the patient from a measurement instrument to the surgical device.

The operator proceeds to locate the limbus 34 using a graphical user interface (GUI) while viewing the still image of the eye (FIG. 3). By way of example, a reticle 37 is moved in position to coincide with the limbus 34. The reticle size may be changed, including a diameter of a circular reticle, or optionally both minor and major radius of an elliptical reticle. The operator then selects a feature or features 21,22 of the eye 11 to be used by outlining the selected feature or features 21,22 within graphical "feature boxes," and the above process is automatically performed by the "push of a button," which takes only seconds to complete in the exemplary embodiment.

Using the first 32 and second 33 edge images, and knowing the center of the reticle 37 (circle or ellipse), the computer 15 determines coordinates for the selected features 21,22.

Image mapping within each feature 21,22 box is a process of using the transformation described below. By way of example, the process fixes the first edge image 32 and varies the angle of orientation for second edge image 33.

The computer 15 overlays the first 32 and the second 33 edge image with regard to center and compares each point within the feature 21,22 box. Each edge image 32,33 is also compared for different values of $\theta$ to determine maximum matching points. The computer 15 moves the center relation for the edge images 32,33 and seeks to improve its location (center a, b) and value for a $\theta$ orientation. Each feature box or area (pixels within area) is processed before moving the center and is completed for every $\theta$ (typically $-25°\leq\theta\leq+25°$), which will typically cover a patient's eye rotation when moving from an upright to a prone position. Completing the entire process takes less than 30 sec.

The treatment pattern, typically a laser shot pattern, is thus modified to account for eye rotation resulting from the patient's movement from upright to prone position. In addition, an eye tracking feature of the second system 38 can account for eye movement during surgery independently of the camera 18.

The system and method for orienting a corrective prescription as described with reference to FIG. 2 may also be applied in "real time" during the corrective surgical procedure, for example, at predetermined intervals. Any additional, usually incremental, cyclotorsion occurring during the procedure can then be detected and compensated for. This "reorientation" of coordinates is calculated by taking the previously collected image as the "first image" and a newly collected image as the "second image," following the steps as described above. Data for such adjustments can be collected and updated orientational changes calculated substantially continuously throughout the procedure if desired.

By way of further example, code for carrying out the process steps to obtain the image of FIG. 8, and code for carrying out an exemplary embodiment of the above for the steps including the feature coordinate determination through the processing of the feature boxes, are disclosed in provisional application No. 60/270,071, which is hereby incorporated herein by reference.

The present invention also provides a system and method for aligning (registering) pairs of eye images taken at different times. By way of example, images may be taken at:
1. An undilated pupil at centration time on wavefront system
2. A dilated pupil at measurement time on wavefront system, using multiple measurements
3. A dilated pupil on a surgical system following formation of the flap To align at least any two images from a mathematics point of view, it is assumed that there is enough information in each of the images to allow for the precise computation of the translational and rotational offsets between pairs of images such that any two images, by way of example, may be overlaid with acceptably small errors. This condition satisfied, an optimized linear transformation between these image pairs is determined. The transformation is uniquely determined by three parameters: a translation vector $r_0=(a,b)$ (a and b are the x and y coordinates of the translation, respectively) and a rotation angle $\theta$.

Image Processing

The Gauss filter is used to eliminate the noise of both images and is defined as:

$$G(x, y, \sigma_1, \sigma_2) = g(u(x,y), \sigma_1) \cdot g'_v(v(x,y), \sigma_2) \quad 1$$

where $$g(u, \sigma) = \frac{1}{\sqrt{2\pi\sigma^2}} \exp\left(-\frac{u^2}{2\sigma}\right); \qquad g'_v(v, \sigma) = -\frac{v}{\sigma} g(v, \sigma) \quad 2$$

and $$u(x,y) = \cos\theta \cdot x - \sin\theta \cdot y \quad 3$$

$$v(x,y) = \sin\theta \cdot x + \cos\theta \cdot y \quad 4$$

is the rotation of the point (x, y) and θ is the angle of rotation. Here θ is set to be either 0 or π/2, which means the filter will eliminate the noise either in the x direction or the y direction. The standard deviation (σ) determines the shape of the filter.

Let Im(x,y) represent the image data function. Applying the Gauss filter to the image function is equivalent to making the convolution of these two functions.

$$NewIm(x,y)=Im(x,y)*G(x,y,\sigma_1,\sigma_2) \qquad 5$$

Next the threshold ξ is computed.

$$\xi=\lambda\cdot\max|NewIm(x,y)|+(1-\lambda)\cdot\min|NewIm(x,y)| \qquad 6$$

where 0<λ<1. The threshold to the new image file is applied as $$ImN(x, y) = \begin{cases} |New\,Im(x, y)| & \text{if } |New\,Im(x, y)| > \xi \\ \xi & \text{otherwise} \end{cases} \qquad 7$$

A bilinear interpolation method is used to determine the edge point, the following comprising a thin function:

$$P=(1-\alpha)[(1-\beta)P_0+\beta P_2]+\alpha[(1-\beta)P_1+\beta P_3] \qquad 8$$

where gradient vector $$\text{gradient of } Im(x,y)=(\alpha,\beta) \qquad 9$$

and $P_i$ are points in a neighborhood of (x,y).

Image Mapping

After processing both images, the best parameters in this linear transformation should be found. The "best" means that, in a given parameter space, it is desired to find a point (parameters) in that space, such that under these parameters the linear transformation minimizes the error between those pairs of images.

The linear transformation is defined as:

$$\begin{pmatrix} x' \\ y' \end{pmatrix} = \begin{pmatrix} \cos\theta & -\sin\theta \\ \sin\theta & \cos\theta \end{pmatrix}\begin{pmatrix} x-center_x \\ y-center_x \end{pmatrix} + \begin{pmatrix} a \\ b \end{pmatrix} \qquad 10$$

The criterion to find the best transform parameters is to minimize the error:

$$\min_{(a,b,\theta)\in D}\sum_{(x,y)}|ImN_{prior}(x,y)-ImN_{post}(x',y')| \qquad 11$$

The pair ($center_x$, $center_y$) is the coordinate of the center point of the limbus from one image.

$$D=\{(a,b,\theta)|a_1<a<a_2, b_1<b<b_2, \theta_1<\theta<\theta_2\} \qquad 12$$

is the parameter (searching) space. The problem is to determine the center-point coordinate ($center_x$, $center_y$) and the searching space $\{a_1,a_2,b_1,b_2,\theta_1,\theta_2\}$. The limbus is manually located in this embodiment on both images to obtain the center coordinate ($center_x$, $center_y$) from the measurement system, and the center coordinate ($center_{xx}$, $center_{yy}$) from the surgical system. The search region is defined as $$a_1=center_{xx}-k,\ a_2=center_{xx}+k \qquad 13$$

$$b_1=center_{yy}-k,\ b_2=center_{yy}+k \qquad 14$$

where k is a integer. The searching resolution is Δθ=0.5°, and the search range is ±25°; so $\theta_1=-25°$, $\theta_2=+25°$. The summation Σ is taken over a reference area (x,y)∈Ω. The reference area is manually located to satisfy the assumption mentioned above.

Figure 9:
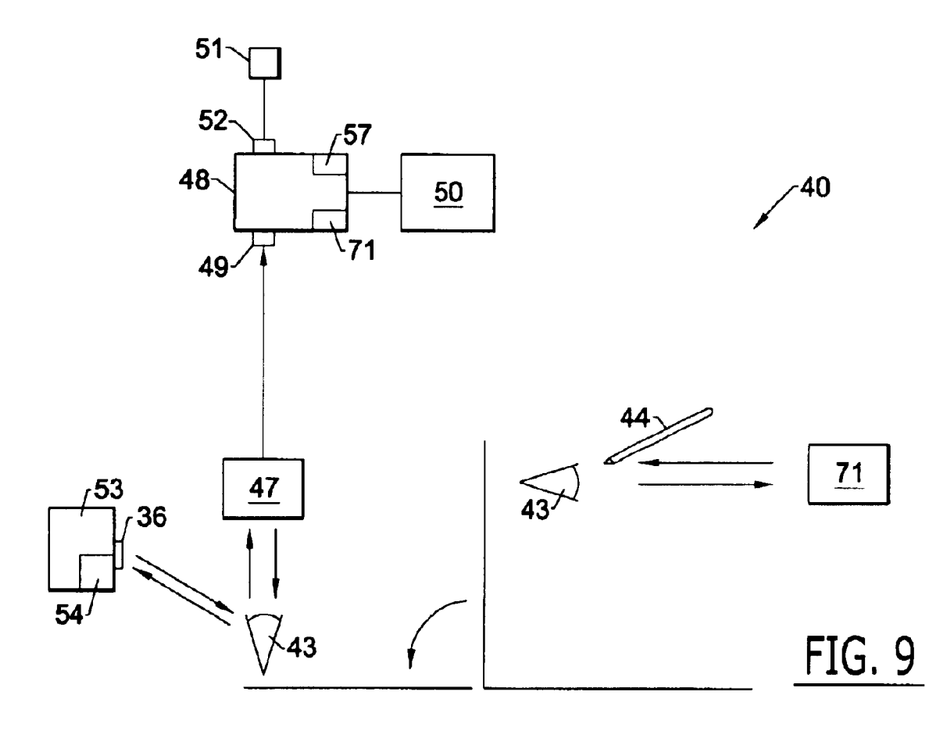
FIG. 9 is a schematic diagram of the system of a second embodiment of the present invention.
Figure 10:
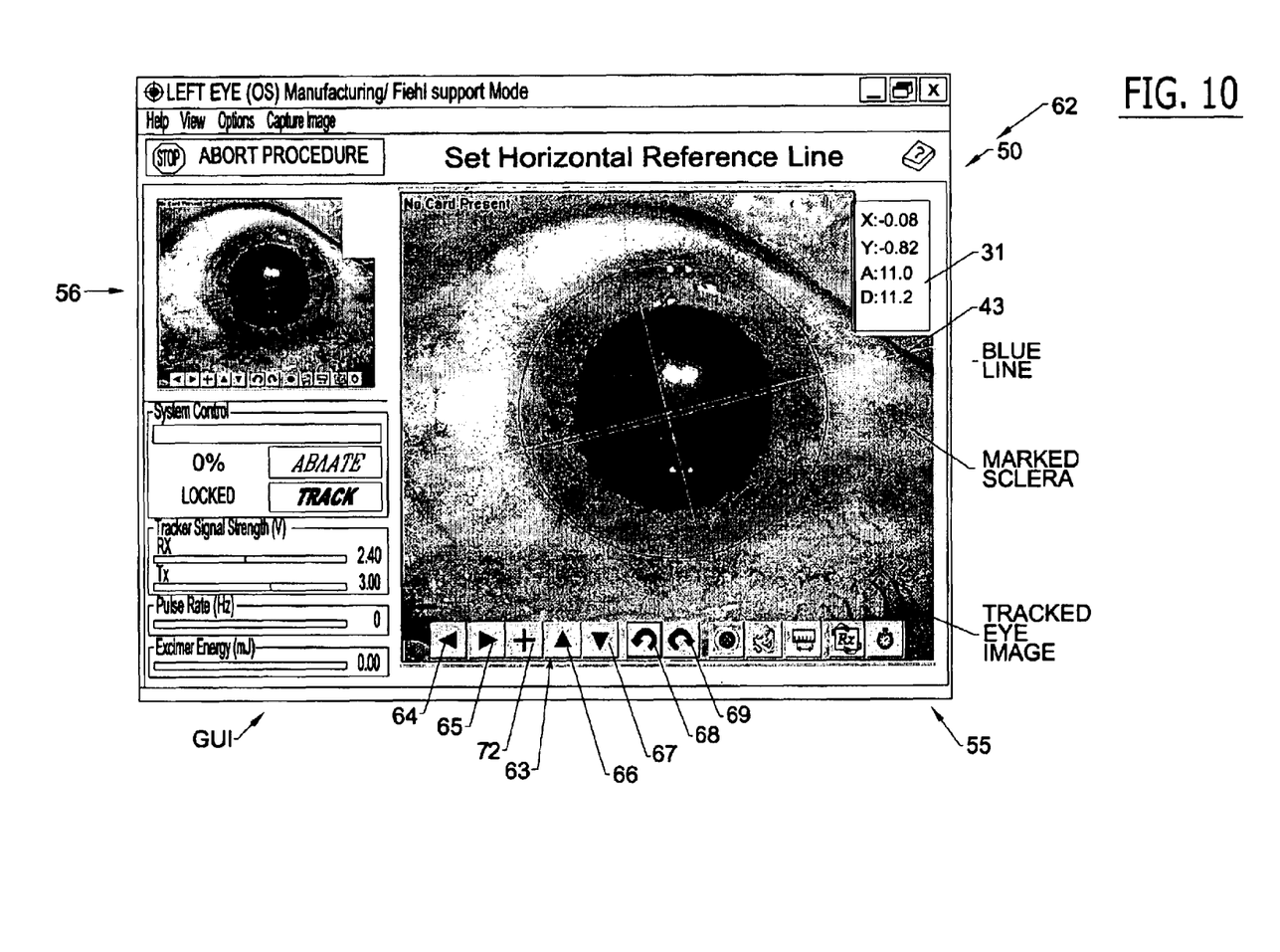
FIG. 10 is a representation of an image of an eye as viewed on a graphical user interface in the second embodiment of the invention.

A second embodiment of the present invention includes an orientation system 40 for eye surgery for correcting at least astigmatism, which is shown schematically in FIG. 9. The graphical user interface and elements thereof are illustrated in FIG. 10. A means for making two alignment marks 41,42 on an eye 43 of a patient (FIG. 10) with the patient in a first position may comprise, for example, an ink pen 44, although this is not intended as a limitation, and alternative marking means known in the art may also be used. In current use, the first position typically comprises a seated upright position. In a preferred embodiment, the alignment marks 41,42 are made at the "3 o'clock" and "9 o'clock" positions to the eye's sclera 45 just outside the margin of the limbus 46. In other words, the alignment marks 41,42 are made at approximately the π/2 and 3π/2 radial positions relative to the limbus 46, with a 0 radial position comprising a top point of the limbus 46. Thus the alignment marks 41,42 are made substantially collinear with a diameter of the limbus 46. One of skill in the art will recognize that these values are exemplary only, and that other locations can be used with similar results.

A camera, preferably a color video camera 47, is provided for imaging the eye with the patient in a second position different from the first position. Typically the second position comprises a prone position.

The system 40 (FIG. 9) also comprises a computer 48 that has input and output means. One input 49 is in electronic connection with the camera 47. Means are also in communication with the computer's input and output means for displaying the eye image to an operator via, for example, a graphical user interface (FIG. 10). Display hardware may comprise, for example, a color video display monitor 50. An operator input device, which may comprise, for example, a mouse 51, is also in electronic communication with another input 52 to the computer 48. Alternatively, other operator input devices may be contemplated; for example, the monitor 50 may comprise a touch screen.

In a preferred embodiment, a corrective system 53 to be used in performing surgery, for example, laser ablation surgery on the cornea, comprises an eye tracker 54 as known in the art. In this embodiment, the monitor 50 displays both a tracked eye image 55 and an untracked eye image 56 (FIG. 10).

A first software routine 57 is resident in the computer 48 for routing the eye images to the monitor 50 and also for superimposing a graphical reticle 58 onto the tracked eye image 55. The first software routine 57 further permits the graphical reticle 58 to be moved by the operator under control of the mouse 51. The graphical reticle 58 comprises a circle 59 for superimposing on the eye's limbus 46 and a cross-hair including a pair of perpendicular lines 60,61, both of which are substantially diametric with the circle 59. Typically the generally horizontal line 60 is used to align with the alignment marks 41,42 on the eye 43. In a color system, the graphical reticle 58 comprises a color for contrasting with the eye 43, such as, but not limited to, yellow.

The monitor 50 preferably is adapted to display a graphical user interface 62 (FIG. 10) that has an interactive control sector 63 thereon. It will be understood by one of skill in the art that this graphical user interface is exemplary only, and that any number of such interfaces may be envisioned so long as the ability to align reticles is provided.

As shown in the exemplary screen of FIG. 10, the control sector 63 comprises a plurality of control sectors, in the form of "buttons," the activation of which moves the graphical reticle 58 in a desired direction. Here the buttons comprise two for horizontal movement, "left" 64 and "right" 65, two for vertical movement, "up" 66 and "down" 67, and two for rotation, counterclockwise 68 and clockwise 69. Clicking on these buttons 64-69 with the mouse 51 causes motion of the graphical reticle 58 on the interface 62 in the indicated direction, as mediated by the first software routine 57 (see rotated graphical reticle in FIG. 10).

In addition, a button 72 performs recentering of the lines 60,61 over the cornea.

A second software routine 71 is also resident in the computer 48 for calculating an orientational change to be applied to a corrective surgical procedure. The procedure, also resident in the computer 48, is to be performed on the eye 43 with the patient in the second position. Such a procedure may comprise, for example, an ablation correction profile that had been determined by a measurement system 71 in electronic communication with the computer 48, with the patient in the first position.

It will be understood based on the teachings of the present invention that in addition to images viewed on the surface of the eye, the position of the retina and any movement thereof may be determined using the above methods to view images on the retina. By way of example, the video camera may be replaced by a scanning laser ophthalmoscope, as disclosed in U.S. Pat. No. 6,186,628 to Van de Velde, which disclosure is hereby incorporated by reference; a retinal nerve fiber layer analyzer, as disclosed in U.S. Pat. No. 5,303,709 to Dreher et al., which disclosure is hereby incorporated by reference; or a fundus camera to provide images of blood vessel patterns that can be used in the same manner as scleral blood vessels as herein described.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A method for orienting a corrective prescription for eye surgery comprising the steps of:

filtering a first image map of an eye of a patient at a first time during the surgery to reduce noise;

processing the filtered first image map to produce a first edge image of the eye in two dimensions;

filtering a second image map of the patient eye at a second time during the surgery to reduce noise;

processing the filtered second image map to produce a second edge image of the eye in two dimensions;

selecting two identifiable features from one of the first and the second image maps;

correlating a location of the two features in the first and the second edge images; and calculating from the correlated locations an orientational change to be applied to a previously determined corrective prescription for a correction profile to be achieved on the eye during the surgery.

2. The method recited in claim 1, wherein the first and the second image maps comprise a first and a second video image captured with one of a charge-coupled-device camera, a scanning laser ophthalmoscope, and a retinal nerve fiber layer analyzer.

3. The method recited in claim 1, wherein the selected eye features comprise portions of at least one blood vessel in a sclera of the eye.

4. The method recited in claim 1, wherein the filtering steps comprise applying a Gauss filter to the first and the second image map and forming, from the first and the second filtered image maps, a first and a second filtered intensity profile.

5. The method recited in claim 4, wherein the first and the second image map processing steps further comprise applying a threshold to the first and the second filtered intensity profiles to produce a first and a second thresholded image.

6. The method recited in claim 5, wherein the first and the second image map processing steps further comprise applying a thin function to the first and the second thresholded image to form the first and the second edge images.

7. The method recited in claim 1, wherein the first and the second filtered intensity profile forming steps comprise:

applying the Gauss filter to the first and the second intensity profiles at a first angle to form a first and a third modified intensity profile;

applying the Gauss filter to the first and the second intensity profiles at a second angle substantially perpendicular to the first angle to form a second and a fourth modified intensity profile;

averaging the first and the second modified intensity profiles to form the first filtered intensity profile; and averaging the third and the fourth modified intensity profiles to form the second filtered intensity profile.

8. The method recited in claim 1, wherein the surgical procedure comprises achieving a desired corneal profile using an excimer laser, and the orientational change calculating step comprises reorienting a coordinate system of the laser to compensate for eye movement between the first and the second time.

9. The method recited in claim 1, wherein the processing, selecting, correlating, and calculating steps are performed at predetermined intervals throughout the surgery, in order to detect orientational changes on a substantially continual basis and permit substantially "real-time" application of the orientational change to the correction profile.

10. A computer-readable medium encoded with a software package for orienting a corrective prescription for eye surgery, the software package comprising:

a code segment for filtering a first image map of an eye of a patient at a first time during the surgery to reduce noise;

a code segment for processing the filtered first image map to produce a first edge image of the eye in two dimensions;

a code segment for filtering a second image map of the patient eye at a second time during the surgery to reduce noise;

a code segment for processing the filtered second image map to produce a second edge image of the eye in two dimensions;

a code segment for correlating a location of two selected identifiable features from one of the first and the second image maps between the first and the second edge images; and a code segment for calculating from the correlated locations an orientational change to be applied to a previously determined corrective prescription for a correction profile to be achieved on the eye during the surgery.

11. The computer-readable medium recited in claim 10, wherein the filtering code segment comprises a code segment for applying a Gauss filter to the first and the second image map and for forming, from the first and the second filtered image maps, a first and a second filtered intensity profile.

12. The computer-readable medium recited in claim 11, wherein the first and the second image map processing code segments further comprise code segments for applying a threshold to the first and the second filtered intensity profiles to produce a first and a second thresholded image.

13. The computer-readable medium recited in claim 12, wherein the first and the second image map processing code segments further comprise code segments for applying a thin function to the first and the second thresholded image to form the first and the second edge images.

14. The computer-readable medium recited in claim 11, wherein the first and the second filtered intensity profile forming code segment comprises:

a code segment for applying the Gauss filter to the first and the second intensity profiles at a first angle to form a first and a third modified intensity profile;

a code segment applying the Gauss filter to the first and the second intensity profiles at a second angle substantially perpendicular to the first angle to form a second and a fourth modified intensity profile;

a code segment averaging the first and the second modified intensity profiles to form the first filtered intensity profile; and a code segment averaging the third and the fourth modified intensity profiles to form the second filtered intensity profile.

15. The computer-readable medium recited in claim 10, wherein the surgical procedure comprises achieving a desired corneal profile using an excimer laser, and the orientational change calculating code segment comprises a code segment for reorienting a coordinate system of the laser to compensate for eye movement between the first and the second time.

16. The computer-readable medium recited in claim 10, wherein the processing, correlating, and calculating code segments are performed at predetermined intervals throughout the surgery, in order to detect orientational changes on a substantially continual basis and permit substantially "real-time" application of the orientational change to the correction profile.

17. A system for orienting a corrective prescription for eye surgery comprising:

means for filtering a first image map of an eye of a patient at a first time during the surgery to reduce noise;

means for processing the filtered first image map to produce a first edge image of the eye in two dimensions;

means for filtering a second image map of the patient eye at a second time during the surgery to reduce noise;

means for processing the filtered second image map to produce a second edge image of the eye in two dimensions;

means for selecting two identifiable features from one of the first and the second image maps;

means for correlating a location of the two features in the first and the second edge images; and means for calculating from the correlated locations an orientational change to be applied to a previously determined corrective prescription for a correction profile to be achieved on the eye during the surgery.

18. The system recited in claim 17, further comprising means for controlling the processing, selecting, correlating, and calculating means to be performed at predetermined intervals throughout the surgery, in order to detect orientational changes on a substantially continual basis and permit substantially "real-time" application of the orientational change to the correction profile.

19. A method for orienting a corrective prescription for eye surgery comprising the steps of:

filtering a first image map of an eye of a patient at a first time during the surgery to reduce noise;

processing the filtered first image map to produce a first edge image of the eye in two dimensions;

filtering a second image map of the patient eye at a second time during the surgery to reduce noise;

processing the filtered second image map to produce a second edge image of the eye in two dimensions;

selecting two identifiable features from one of the first and the second image maps;

correlating a location of the two features in the first and the second edge images; and calculating from the correlated locations an orientational change to be applied to a previously determined corrective prescription for a correction profile to be achieved on the eye during the surgery;

wherein the processing, selecting, correlating, and calculating steps are performed at predetermined intervals throughout the surgery, in order to detect orientational changes on a substantially continual basis and permit substantially "real-time" application of the orientational change to the correction profile.

20. A computer-readable medium encoded with a software package for orienting a corrective prescription for eye surgery, the software package comprising:

a code segment for filtering a first image map of an eye of a patient at a first time during the surgery to reduce noise;

a code segment for processing the filtered first image map to produce a first edge image of the eye in two dimensions;

a code segment for filtering a second image map of the patient eye at a second time during the surgery to reduce noise;

a code segment for processing the filtered second image map to produce a second edge image of the eye in two dimensions;

a code segment for correlating a location of two selected identifiable features from one of the first and the second image maps between the first and the second edge images; and a code segment for calculating from the correlated locations an orientational change to be applied to a previously determined corrective prescription for a correction profile to be achieved on the eye during the surgery;

wherein the processing, correlating, and calculating code segments are performed at predetermined intervals throughout the surgery, in order to detect orientational changes on a substantially continual basis and permit substantially "real-time" application of the orientational change to the correction profile.

21. A system for orienting a corrective prescription for eye surgery comprising:

means for filtering a first image map of an eye of a patient at a first time during the surgery to reduce noise;

means for processing the filtered first image map to produce a first edge image of the eye in two dimensions;

means for filtering a second image map of the patient eye at a second time during the surgery to reduce noise;

means for processing the filtered second image map to produce a second edge image of the eye in two dimensions;

means for selecting two identifiable features from one of the first and the second image maps;

means for correlating a location of the two features in the first and the second edge images;

means for calculating from the correlated locations an orientational change to be applied to a previously determined corrective prescription for a correction profile to be achieved on the eye during the surgery; and means for controlling the processing, selecting, correlating, and calculating means to be performed at predetermined intervals throughout the surgery, in order to detect orientational changes on a substantially continual basis and permit substantially "real-time" application of the orientational change to the correction profile.

22. A method for orienting a corrective prescription for eye surgery comprising the steps of:

processing a first image map of an eye of a patient at a first time during the surgery to produce a first edge image of the eye in two dimensions;

processing a second image map of the patient eye at a second time during the surgery to produce a second edge image of the eye in two dimensions;

selecting two identifiable portions of at least one blood vessel in a sclera of the eye from one of the first and the second image maps;

correlating a location of the two features in the first and the second edge images; and calculating from the correlated locations an orientational change to be applied to a previously determined corrective prescription for a correction profile to be achieved on the eye during the surgery.

23. The method recited in claim 22, wherein the first and the second image map processing steps comprise filtering the first and the second image map, respectively, to reduce noise.

24. The method recited in claim 23, wherein the filtering steps comprise applying a Gauss filter to the first and the second image map and forming, from the first and the second filtered image maps, a first and a second filtered intensity profile.

25. The method recited in claim 24, wherein the first and the second image map processing steps further comprise applying a threshold to the first and the second filtered intensity profiles to produce a first and a second thresholded image.

26. The method recited in claim 25, wherein the first and the second image map processing steps further comprise applying a thin function to the first and the second thresholded image to form the first and the second edge images.

27. The method recited in claim 22, wherein the first and the second filtered intensity profile forming steps comprise:

applying the Gauss filter to the first and the second intensity profiles at a first angle to form a first and a third modified intensity profile;

applying the Gauss filter to the first and the second intensity profiles at a second angle substantially perpendicular to the first angle to form a second and a fourth modified intensity profile;

averaging the first and the second modified intensity profiles to form the first filtered intensity profile; and averaging the third and the fourth modified intensity profiles to form the second filtered intensity profile.

* * * * *